(12) United States Patent
Eggink et al.

(10) Patent No.: US 9,981,044 B2
(45) Date of Patent: May 29, 2018

(54) ACTIVATION OF ADAPTIVE IMMUNE PROCESSES FOR THE TREATMENT OF CANCERS AND INFECTIOUS DISEASES

(71) Applicant: Susavion Biosciences, Inc., Tempe, AZ (US)

(72) Inventors: Laura L. Eggink, Scottsdale, AZ (US); J. Kenneth Hoober, Phoenix, AZ (US)

(73) Assignee: Susavion Biosciences, Inc., Tempe, AZ (US)

( * ) Notice: Subject to any disclaimer, the term of this patent is extended or adjusted under 35 U.S.C. 154(b) by 0 days. days.

(21) Appl. No.: 15/507,639

(22) PCT Filed: Aug. 31, 2015

(86) PCT No.: PCT/US2015/047794
§ 371 (c)(1),
(2) Date: Feb. 28, 2017

(87) PCT Pub. No.: WO2016/033602
PCT Pub. Date: Mar. 3, 2016

(65) Prior Publication Data
US 2017/0290922 A1   Oct. 12, 2017

Related U.S. Application Data

(60) Provisional application No. 62/044,238, filed on Aug. 30, 2014.

(51) Int. Cl.
*A61K 38/08* (2006.01)
*A61K 47/65* (2017.01)
(Continued)

(52) U.S. Cl.
CPC ........ *A61K 47/48246* (2013.01); *A61K 38/08* (2013.01); *A61K 38/19* (2013.01); *A61K 47/641* (2017.08); *A61K 47/65* (2017.08); *C07K 14/47* (2013.01); *C07K 14/52* (2013.01); *G01N 33/574* (2013.01); *A61K 38/00* (2013.01); *A61K 39/00* (2013.01); *C07K 19/00* (2013.01); *C07K 2319/02* (2013.01)

(58) Field of Classification Search
CPC ........ A61K 38/08; A61K 47/50; A61K 47/62; A61K 47/64; A61K 47/65; A61K 47/641; C07K 7/06
See application file for complete search history.

(56) References Cited

U.S. PATENT DOCUMENTS 8,496,942 B2   7/2013   Eggink et al.
2010/0286040 A1   11/2010   Eggink et al.
2014/0155313 A1   6/2014   Eggink et al.

FOREIGN PATENT DOCUMENTS

WO   2013/096829 A2   6/2013

OTHER PUBLICATIONS

Eggink et al., "Peptide Mimetics of Terminal Sugars of Complex Glycans", Glycobiology Insights, 2:1-12 (2010).

*Primary Examiner* — Jeffrey E. Russel
(74) *Attorney, Agent, or Firm* — Rodney J. Fuller; Booth Udall Fuller, PLC

(57) ABSTRACT

Polypeptides, such as a multi-valent polypeptide designated svD2, useful in pharmaceutical compositions for stimulation of the adaptive arm of the immune system. svD2 demonstrated in vivo activity in a syngeneic mouse model. svD2 is biologically active at nanomolar concentrations. These properties are believed to result as a consequence of the ability of svD2 to cross-link cell-surface receptors.

18 Claims, 9 Drawing Sheets

(51) Int. Cl.
*A61K 47/48* (2006.01)
*C07K 14/47* (2006.01)
*C07K 14/52* (2006.01)
*A61K 38/19* (2006.01)
*G01N 33/574* (2006.01)
*A61K 47/64* (2017.01)
*A61K 38/00* (2006.01)
*A61K 39/00* (2006.01)
*C07K 19/00* (2006.01)

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 1

Val Ser Asn Gln His
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 2

Val Ser Asn Gln His Gly Gly Gly Ser
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 3

Gly Gly Gly Ser
1
```

ACTIVATION OF ADAPTIVE IMMUNE PROCESSES FOR THE TREATMENT OF CANCERS AND INFECTIOUS DISEASES

CROSS REFERENCE TO RELATED APPLICATIONS

This application is the U.S. National Stage of International Application No. PCT/US2015/047794, filed on Aug. 31, 2015, which claims priority to and the benefit of U.S. Provisional Patent Application No. 62/044,238 filed on Aug. 30, 2014, the contents of each of which are incorporated herein by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 848 kilobyte ASCII (text) file named "Seq_list" created on Feb. 28, 2017.

FIELD OF THE INVENTION

The present invention relates to polypeptides that activate the adaptive immune response by stimulating development of B cells and B memory cells.

BACKGROUND

It is remarkable that each one of us carries pathogens such as viruses, bacteria and cancer cells in our bodies, yet we are able to go about our daily lives without worry because our immune system keeps most pathogens in check. So, why does a person become afflicted with cancer or another disease?

The immune system consists of two broadly-defined 'branches,' the innate, cellular defense mechanism, defined loosely as Th1, and the adaptive, humoral or antibody-dependent system, defined as Th2. The latter process generates antibodies against antigens derived from digestion of pathogens by phagocytic cells of the innate system. Critical to the development of the Th2 response is activation of the antibody-producing B cells and their differentiation into memory B cells that retain the ability to respond to subsequent challenges from an antigen.

Theoretically, the immune system should be able to mount a response to any type of cancer as well as infectious agents that have unique structures. Activation of immune cells to generate endogenous vaccines, i.e., autovaccination, promotes use of the body's powerful antibody-producing mechanisms against cancer cells and other infective agents. Rather than employing techniques that are effective against specific types, autovaccination should achieve a broad spectrum capacity, i.e., a technology that can be used for multiple types of cancer. However, to achieve this goal, the cell-mediated branch of the immune system must be activated, within which are the antibody-producing memory B cells. Destruction of cancer cells then occurs by antibody-dependent cellular cytotoxicity (ADCC) performed by macrophages, neutrophils and natural killer cells.

Thus in most cases of a person being afflicted with cancer, the person's immune system has been weakened, for example by stress, illness malnutrition, or age. A weakened immune system allows infective agents such as viruses or bacteria that may have been latent for many years to emerge and cause disease, including cancer. In addition, the infective agent or cancer cell may have learned how to evade the immune system's defenses. These pathogens can achieve this "escape" in a number of ways. For cancer cells, they can either suppress the immune system or make themselves look like normal tissues.

Although fighting bacterial infections with "antibiotics" has been relatively easy, because bacteria are easy, non-human targets for drugs that are relatively safe and easy to use. And even when the bacteria become resistant to the "antibiotic," there are other "antibiotics" available. On the other hand, treating cancers and viral infections has not been easy. Not only do these treatments target human processes, and thus tend to be quite toxic, they are also susceptible to resistance. Therefore, there is a need for treatments that overcome the ability of pathogens, for example cancer cells, to "escape." In particular, there is a need for drugs that expand, mature, and activate the immune system and, most importantly, do not have the toxic effects are caused by chemotherapy drugs and antibody therapies.

Immunotherapy has had an uneven history with periods of hope followed by periods of disappointment. However, recently new approaches have again opened options for therapy that have caused great enthusiasm, so much so that Science Magazine in December 2013 called cancer immunotherapy "Breakthrough of the Year." This declaration followed the successful use of monoclonal antibodies against certain cancers, in particular melanoma. In contrast to the polyclonal response of the endogenous immune system, treatment with a monoclonal antibody targets a single antigen. Monoclonal antibodies have been developed to block inflammation and the activity of angiogenic cytokines to reduce blood flow into tumors. The most dramatic antibiotics therapies have been antibodies against inhibitory receptors on T cells such as CTLA-4 and PD-1 Inhibition of the function of these receptors leads to enhanced activity of cytotoxic T cells, which are capable of killing cancer cells. In addition, inhibition of CTLA-4 causes a reduction in inhibitory, regulatory T cells by binding to this receptor, which is expressed at elevated levels in tumors and thereby marks these cells for destruction by macrophages. The use of these antibodies is still accompanied by serious toxic side-effects, which often must be controlled by anti-inflammatory steroids.

Accordingly, there is a need in the art for improved methods for the treatment of diseases and condition where the pathogen "escapes" the immune response (for example cancers), at least in terms of prolonging subject survival and/or quality of life.

SUMMARY OF THE INVENTION

The present invention is directed to methods for treating cancers such as ovarian and melanoma; for increasing the survival period of a subject diagnosed as having a tumor; and/or for increasing the survival rate of a subject diagnosed as having a tumor. The methods of the invention involve enhancing the adaptive immune system of a subject by administering to the subject a polypeptide that induces a greater release of the cytokine IL-21 in a cytokine release assay than IFNγ. In preferred embodiments, the polypeptide comprises an amino acid sequence of VSNQH (SEQ ID NO:1). In some implementations, the methods may comprise administering branched versions of the polypeptide, such as having multiple arms. In some aspects, at least one arm of the branched polypeptide comprises the sequence VSNQHGGGS (SEQ ID NO:2). In a preferred embodiment, the branched polypeptide has a multivalent structure (e.g., a tetravalent structure) with multiple arms (e.g., four arms) having SEQ ID NO:2 in each arm. The arms may extend be extended from lysine residues. In the case of branched polypeptides, active portions of the sequences may occur at the amino-terminal or carboxyl-terminal ends of the arms. The distances of these active portions of the sequences from the branch junctions may be altered, using various spacer portions of the sequences, to achieve the desired conformation of the polypeptide, particularly with respect to orienting the active polypeptide sequences in such a manner to achieve high affinity/association with ligands of cell-surface receptors. A representative spacer sequence, as a portion of a sequence of SEQ ID NO:2 above, is GGGS (SEQ ID NO:3).

The stimulation of the adaptive immune system may be marked by increased density of one or more cellular markers on peritoneal cells. The markers include one or more of CD19, CD8, NK1.1, and CD69. In preferred embodiments, the stimulation of the adaptive immune system is marked by stimulated development of B cells and B memory cells.

The polypeptide may be administered systemically, subcutaneously, or sublingually. In preferred implementations, the polypeptide is administered in an aqueous pharmaceutical composition having a polypeptide concentration from about 0.1 to about 10 mM and a pharmaceutically acceptable carrier. In these embodiments, the pharmaceutical composition is administered by subcutaneous injection or by a sublingual application.

The dose of the polypeptide administered to a subject may at least about 10 µg/kg body weight or at least 0.1 nmol/g body weight. For example, those dose may be about 10 µg/kg body weight to about 5 mg/kg body weight per dose about 5 mg/kg body weight per dose or about 0.1 nmol/g body weight to about 1 nmol/g body weight.

The polypeptide may be administered to bind to receptors on immune cells. In a first aspect, the polypeptide stimulates the production of progenitor/precursor cells in the peritoneal cavity. In a second aspect, the polypeptide induces maturation and activation of immune cells in the peritoneal cavity. In a third aspect, the polypeptide causes an increase in mature cells, including T and B lymphocytes, cytotoxic T cells and natural killer cells. In a fourth aspect, the polypeptide may also stimulate migration of mature immune cells from the peritoneal cavity into the blood. The polypeptide may also stimulate release of cytokines beneficial for destruction of cancer cells or an infectious agent. The beneficial cytokines include eotaxin, IL-17, IL-21, TNF-$\alpha$, lymphotoxin-$\alpha$ (TNF-$\beta$), and MCP-2. The polypeptide does not stimulate phagocytosis, based on comparison of internalization of bacterial cells by PBMCs stimulated with IFN$\gamma$.

In some implementations of the present invention, the polypeptide is administered as a complement to another therapy. The polypeptide may also be administered in multiple doses over a treatment regimen. For example, the polypeptide is administered on alternate days during the treatment regimen or administered one or two times per week during the treatment regimen.

These and other embodiments and aspects relating to the present invention are apparent from the following Detailed Description.

BRIEF DESCRIPTION OF THE DRAWINGS

FIGS. 1-7 are to be understood to present illustrations of some embodiments of the invention and/or principles involved. These embodiments are illustrated in FIGS. 1-7 by way of example, and not by way of limitation.

DETAILED DESCRIPTION

The present invention is directed to a unique, innovative approach to stimulate the immune system that is not another toxic agent to put into the subject's body. Rather the present invention is direct to methods of stimulating the immune system by providing the immune system with the power to overcome the assaults from cancer and infectious agents. In particular, the present invention is directed to the stimulated development of B cells and B memory cells. The present invention relates to peptides that bind and activate lectin-type receptors and amplify the ability of the immune system to defend against diseases such as cancer and viral and bacterial infections. These peptides restore the ability of the immune system to overcome the ability of cancers and other infectious agents to escape and cause disease. Application of this approach provides an enhanced, natural defense against disease. Specifically, the present invention is directed an approach of treating cancers, such as ovarian cancer or melanoma, in a subject by administering to the subject a polypeptide comprising an amino acid sequence of VSNQH (SEQ ID NO:1). Such methods may also involve conventional surgery and/or radiation and/or immunotherapeutic monoclonal antibodies as part of an overall treatment regimen.

The single letter designation for amino acids is used in this disclosure. According to art-recognized convention, such single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

The present invention is also directed to polypeptides having the amino acid sequence of VSNQH (SEQ ID NO:1) in a branched form. Branching beneficially provides polypeptides with a multivalent structure (e.g., having multiple amino acid sequences, as described above, that impart greater binding avidity of the polypeptide to receptors of immune system cells). Each of the multiple arms may extend from residues of the same type or different types of amino acid. For example, each arm (or a subset of the arms) may extend from lysine residues. The branched polypeptide optionally further includes a valine residue and/or a spacer sequence bonded to the respective N-terminal and/or C-terminal ends of such sequences. For example, an arm of the branched peptide comprising the amino acid sequence of VSNQH (SEQ ID NO:1) may have an amino acid sequence of VSNQHGGGS (SEQ ID NO:2). Branched polypeptides may have 2, 3, 4, or more arms, at least one of which, some portion of which, or all of which, comprise(s) the active mimetic sequence of SEQ ID NO:1, including sequences having additional C-terminal, N-terminal, and/or spacer sequences.

Figure 1A:
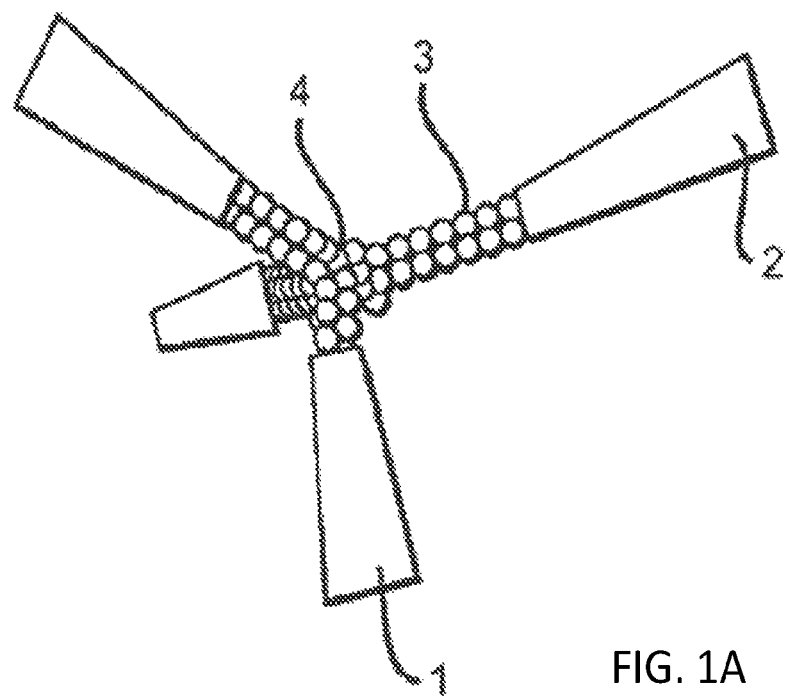
FIG. 1A depicts a tetravalent polypeptide, having four 'arms', each terminating with a polypeptide sequence (1, 2), with the active sequences being spaced apart from a tri-lysine core (4) using spacer sequences (3).
Figure 1B:
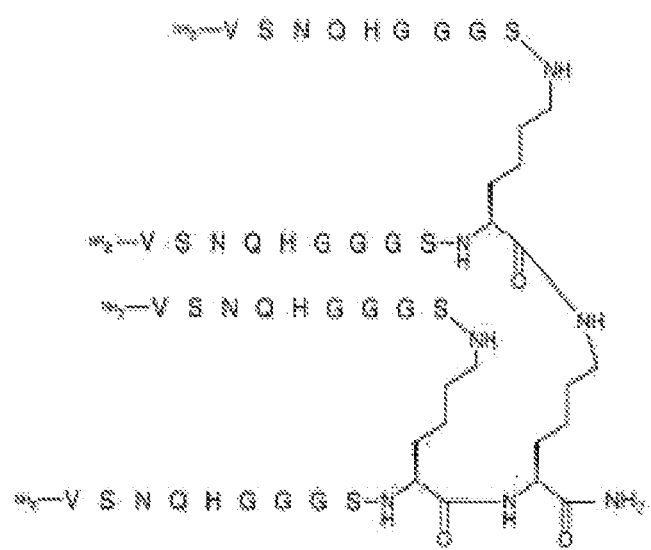
FIG. 1B shows a particular tetravalent polypeptide, designated svD2, of the type depicted in FIG. 1A, with each of the four arms extending from the tri-lysine core and having identical polypeptide sequences.
Figure 2:
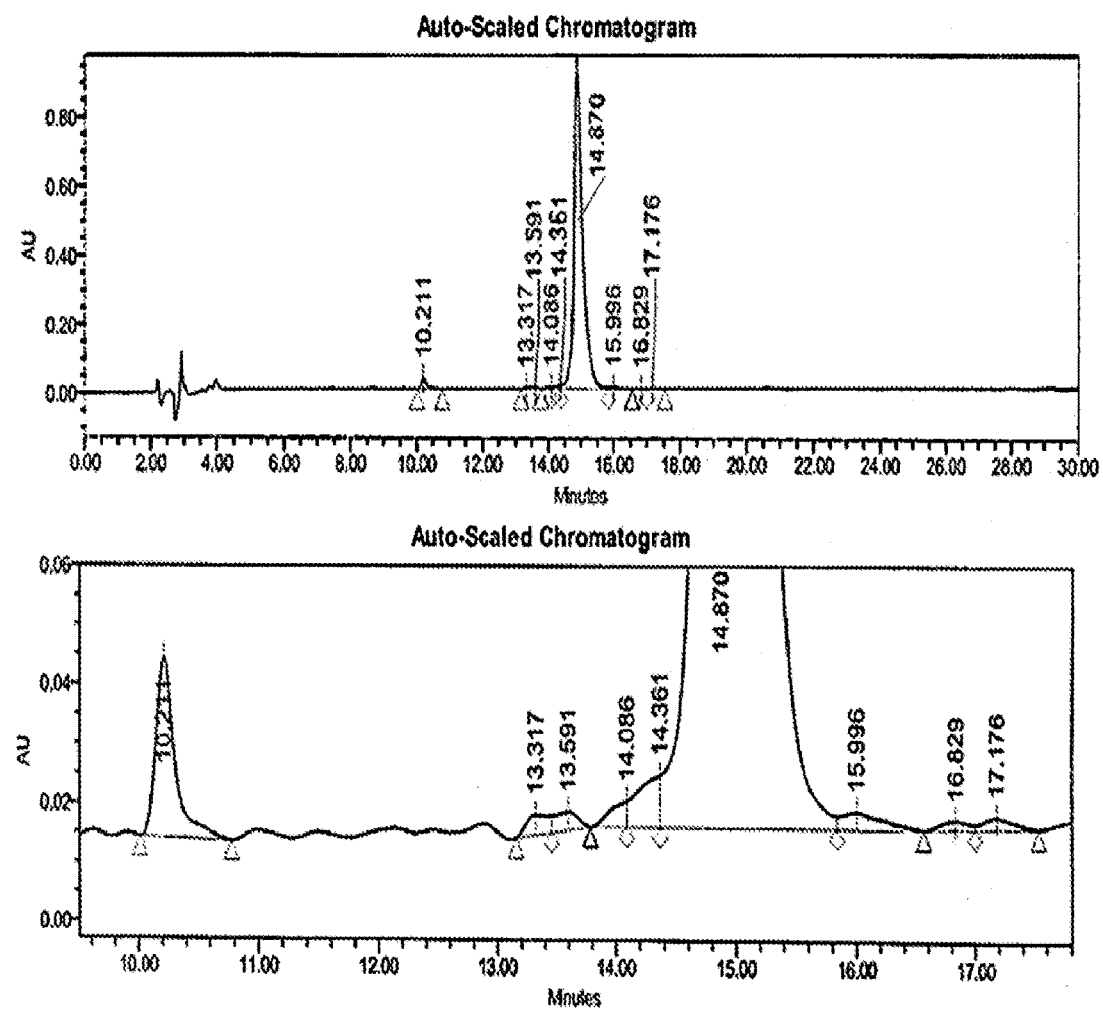
FIG. 2 is an HPLC chromatogram of purified svD2.

A schematic representation of a polypeptide having four arms, each with an active mimetic sequence 1 and a spacer sequence 2 linking the mimetic sequence 1 to the polypeptide core 3 (e.g., a tri-lysine core), is illustrated in FIG. 1A. The chemical structure of a specific polypeptide with 4 arms, each having the polypeptide sequence of SEQ ID NO:2, comprising both active mimetic and spacer sequences, is illustrated in FIG. 1B. As shown, this polypeptide has a C-terminal amide group. The arms of this tetravalent polypeptide extend from a tri-lysine core, providing the sequence [(VSNQHGGGS)$_2$K]$_2$K-NH$_2$ (SEQ ID NO:2, see FIG. 1B). The polypeptide consisting of the amino sequence of SEQ ID NO: 2 is designated throughout this disclosure as svD2. Other polypeptides according to the present invention comprise elements of this sequence.

Polypeptides may generally comprise natural or synthetic amino acids, amino acid analogs, or peptidomimetics, which are normally bonded by peptide bonds. Such synthetic amino acids, analogs, or mimetics may replace one or more naturally occurring amino acids in the active amino acid sequences, as described herein, or may replace one or more naturally occurring amino acids elsewhere in the polypeptide. The polypeptides are synthesized chemically. Amino acid sequences as described above may be present in these polypeptides in a single copy or in multiple copies (e.g., 2 or more copies, such as between 2 and 10 copies, or between 2 and 6 copies). In exemplary embodiments, copies of the amino acid sequences are present in separate branches to provide a branched configuration with multiple functionality due to the multiple copies (i.e., as in the case of a multivalent branched polypeptide). These polypeptides may be prepared by known methods such as those described herein and also in *Solid Phase Peptide Synthesis: A Practical Approach* (B. Atherton and R. C. Sheppard, eds., 1989. Oxford University Press, New York, N.Y.); *Solid-Phase Synthesis: A Practical Guide* (S. A. Kates and F. Albericio, eds., 2000. Marcel Dekker, Inc., New York, N.Y.); *Fmoc Solid Phase Peptide Synthesis: A Practical Approach* (W. C. Chan and P. D. White, eds., 2000. Oxford University Press, New York, N.Y.). The synthesis of branched polypeptides is described in D. N. Posnett, H. McGrath, and J. P. Tam (1988); *A novel method for producing anti-peptide antibodies*, JOURNAL OF BIOLOGICAL CHEMISTRY 263: 1719-1725.

Synthetic polypeptides, prepared using known solid phase, liquid phase, or peptide condensation techniques, or any combination thereof, can include natural and synthetic (unnatural) amino acids. Amino acids used for polypeptide synthesis may be Boc (N-α-amino protected N-α-t-butyloxycarbonyl) amino acid resin with the standard deprotecting, neutralization, coupling and wash protocols of the original solid phase procedure of Merrifield (1963, J. AM. CHEM. SOC. 85: 2149-2154), or the base-labile N-α-amino protected 9-fluorenylmethoxycarbonyl (Fmoc) amino acids first described by Carpino and Han (1972, J. ORG. CHEM. 37:3403-3409). Both Fmoc and Boc N-α-amino protected amino acids can be obtained, for example, from Sigma-Aldrich, Cambridge Research Biochemical or CBL Biopharma. In addition, the polypeptides can be synthesized with other known N-α-protecting groups. The peptides were also synthesized with an added C-terminal ε-biotinyl-lysine-amide.

Solid phase polypeptide synthesis may be accomplished by techniques described, for example, in Stewart and Young (1984) SOLID PHASE SYNTHESIS, 2$^{nd}$ Ed., Pierce Chemical Co., Rockford, Ill. or Fields and Noble (1990) INTERNATIONAL JOURNAL OF PEPTIDE AND PROTEIN RESEARCH 35:161-214. Automated synthesizers may also be used. Polypeptides comprising any of the amino acid sequences described herein may comprise the unnatural D-amino acids (resistant to L-amino acid-specific proteases in vivo), including combinations of D- and L-amino acids. These D- and L-amino acids may be present in the active amino acid sequences described herein, or may be present elsewhere in the polypeptide. The polypeptides may comprise various "designer" amino acids (e.g., β-methyl amino acids, C-α-methyl amino acids, and N-α-methyl amino acids, etc.) in the active sequences or elsewhere in the polypeptide to convey special properties. Synthetic amino acids include ornithine for lysine, and norleucine for leucine or isoleucine.

In addition, polypeptides comprising any of the amino acid sequences described herein can have peptidomimetic bonds, such as ester bonds, to prepare polypeptides with novel properties. For example, a polypeptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a peptide bond would be resistant to protease activity, and would possess an extended half-life in vivo.

According to further embodiments, the polypeptides comprising any of the amino acid sequences described herein can be fused or otherwise linked to therapeutic agents in order to enhance potential therapeutic effects of both agents. For example, monoclonal antibodies have been generated against a large number of cancers and other pathogenic agents for therapeutic use. Binding of these antibodies to the infectious agent is the first part of the therapy. Phagocytosis of the antibody-bound agent by macrophages and other phagocytic cells must then occur to eliminate the agent from the body. Therefore, a combination of target-directed antibodies with the polypeptides described herein provides an effective combination therapy. Many other such fusions or linkages to other therapeutic agents will be apparent to those of skill in the art, having regard for the teachings herein.

It will be understood by those of skill in the art that such fusion proteins can result from the addition of a polypeptide having an amino acid sequence as described herein to the carboxy or amino terminal end of another polypeptide, or can comprise the placement of a polypeptide having an amino sequence as described herein within another polypeptide. Those skilled in the art, having regard for the teachings herein, will recognize many such fusion proteins can be made and used.

Polypeptides comprising amino acid sequences as described herein may be modified by, or bound to, non-polypeptide compounds to produce desirable characteristics, such modifications including but not limited to PEGylation with polyethylene glycol to improve in vivo residency time of the polypeptide, alkylation, phosphorylation, acylation, ester formation, amide formation, lipophilic substituent addition, and modification with markers including but not limited to fluorophores, biotin, dansyl derivatives, and radio-active moieties. Such non-polypeptide compounds can be directly linked, or can be linked indirectly, for example via a spacer of β-alanine, gamma-aminobutyric acid (GABA), L/D-glutamic acid, succinic acid or similar structure.

Further embodiments of the present invention relate to pharmaceutical compositions useful in the treatment of cancer, comprising one or more polypeptides having amino acid sequences described herein, and a pharmaceutically acceptable carrier. Representative carriers include adjuvants appropriate for the indicated route of administration. For example, the polypeptides may be admixed with lactose, sucrose, starch powder, cellulose esters of alkanoic acids, stearic acid, talc, magnesium stearate, magnesium oxide, sodium and calcium salts of phosphoric and sulphuric acids, sodium chloride, potassium chloride, acacia, gelatin, sodium alginate, polyvinylpyrrolidine, polyvinylalcohol, dextran sulfate, heparin-containing gels, and/or polyvinyl alcohol, and tableted or encapsulated for conventional administration. Alternatively, the polypeptides may be dissolved in carriers such as physiological saline, water, polyethylene glycol, propylene glycol, carboxymethyl cellulose colloidal solutions, ethanol, corn oil, peanut oil, cottonseed oil, sesame oil, or tragacanth gum, optionally with a physiological buffer system. Other adjuvants and associated modes of administration are known in the pharmaceutical arts. Representative carriers also include time delay materials, such as glyceryl monostearate or glyceryl distearate alone or with a wax, or other known materials. The polypeptides may be covalently or non-covalently bonded to other compounds to promote an increased half-life in vivo, such as polyethylene glycol.

In carrying out representative treatment methods, a pharmaceutical composition comprising the active agent (e.g., a polypeptide as described herein) in a solid form (including granules, powders, transdermal or transmucosal patches or suppositories) or in a liquid form (e.g., solutions, suspensions, or emulsions) may be subjected to conventional pharmaceutical operations such as sterilization and/or may contain conventional pharmaceutically acceptable carriers, such as adjuvants as described above, stabilizers, wetting agents, emulsifiers, preservatives, cosolvents, suspending agents, viscosity enhancing agents, ionic strength and osmolality adjustors, and/or buffering agents. Suitable water soluble preservatives include sodium bisulfite, sodium thiosulfate, ascorbate, benzalkonium chloride, chlorobutanol, thimerosal, phenylmercuric borate, parabens, benzyl alcohol, phenylethanol or antioxidants such as Vitamin E and tocopherol and chelators such as EDTA and EGTA. These preservatives and other carriers may be present in pharmaceutical compositions, generally in an amount from about 0.001% to about 5% by weight, and often from about 0.01% to about 2% by weight.

When a polypeptide is administered, according to methods described herein, to a subject in need of treatment for cancer, preferably the subject is a mammal and more preferably a human. Administration may be by any suitable route, including local delivery, parentally, transdermally, sublingually, inhalation, and topically, in dosage unit formulations containing conventional pharmaceutically acceptable carriers, as described above. Parenteral administration includes subcutaneous, intravenous, intramuscular, intrasternal, intratendinous, intraspinal, intracranial, intrathoracic, intraperitoneal, and infusion techniques. Preferred administration routes are subcutaneous and intravenous injection, as well as buccal and sublingual administration. The concentration of the polypeptide in an aqueous pharmaceutical composition may be about 0.1 mM to about 10 mM. The amount of the polypeptide administered per dose may be at least 10 μg/kg body weight or a least 0.1 nmol/g body weight. In some implementations, the amount of the polypeptide administered per dose may be about 10 μg/kg body weight to about 5 mg/kg body weight or about 0.1 nmol/g body weight to about 1 nmol/g body weight, for example, about 10 μg/kg body weight, about 50 μg/kg body weight, about 100 μg/kg body weight, about 500 μg/kg body weight, about 1 mg/kg body weight, about 2.5 μg/kg body weight, about 5 mg/kg body weight, about 0.1 nmol/g body weight, about 0.15 nmol/g body weight, about 0.25 nmol/g body weight, about 0.5 nmol/g body weight, about 0.75 nmol/g body weight, or about 1 nmol/g body weight.

Methods for the treatment of disease, by administration of therapeutic agents (e.g., polypeptides described herein), can be used as in combination with another therapy. For example, the polypeptide may be administered to the subject to complement surgery on the subject, including primary surgery for removing one or more tumors, secondary cytoreductive surgery, and secondary palliative surgery. In addition to surgery, or in the absence of surgery, the polypeptide may also be administered with at least one other therapeutic agent. The other therapeutic agent may be, for example, a second immunotherapeutic monoclonal antibody, chemotherapeutic agent, or radiation therapy. In some embodiments, administering the therapeutic agent can reduce the chemotherapy and/or radiation dosage necessary to inhibit tumor growth and/or metastasis. The therapeutic agent may be administered prior to, at the time of, or shortly after a given round of treatment with an antibody therapy, a chemotherapy and/or radiation therapy (radiotherapy). Radiation therapy includes external-beam radiation therapy, as well as the use of radiolabeled compounds targeting tumor cells. Any reduction in a chemotherapeutic or a radiotherapeutic dose, as a result of administration of a polypeptide as described herein, benefits the subject by decreasing side effects relative to standard chemotherapy and/or radiation therapy treatment.

Administration of the pharmaceutical composition is performed, according to some embodiments, in conjunction with radiotherapy, the administration of other chemotherapeutic agents, and/or surgical procedures. Those having skill in the art, with the knowledge gained from the present disclosure, will recognize that various changes can be made in these treatment methods without departing from the scope of the present disclosure. For example, in some implementations, the polypeptide would be administered by a subcutaneous injection while in other implementations, the polypeptide would be administered by a sublingual application. In some embodiments, the polypeptide may need to be administered in multiple doses. In these embodiments, the polypeptide may be administered on alternate days during the treatment regimen or administered one to two times per week during the treatment regime.

The following examples are set forth as representative of the present invention. These examples are not to be construed as limiting the scope of the invention as other equivalent embodiments will be apparent in view of the present disclosure and appended claims.

EXAMPLE 1

The tetravalent polypeptide svD2, as described above, was synthesized, purified, and evaluated in terms of physical and biological properties that are important in the pharmaceutical compositions described herein (FIG. 1A).

Synthesis and Purification of svD2

Tetravalent polypeptides were synthesized by general, standard chemistry methods utilizing Fmoc (9-fluorenylmethoxycarbonyl)-protected amino acids. Protecting groups for amino acid sidechains during synthesis were tert-butyl for the hydroxyl group of serine, Boc (tertbutyloxycarbonyl) for the ε-amino group of lysine, PBF (2,2,4,6,7-pentamethyl-2,3-dihydrobenzofuran-5-sulfonyl) for arginine, or trityl for the imidazole group of histidine. The most difficult blocking groups to remove (and the additional mass provided by a residual blocking group) were tert-butyl (56 Da) and PBF (253 Da). The blocking groups were removed by trifluoroacetic acid (TFA) during cleavage from the resin. Modifications at the C-terminus consisted of (a) an amide group (no tag) or (b) an extension of the polypeptide by addition of C-terminal ε-biotinyl-lysine-amide or β-alanine-cysteine-amide. The thiol group on C-terminal cysteine is available for addition of a dansyl group by reaction with 5-((((2-iodoacetyl)amino)ethyl)amino)naphthalene-1-sulfonic acid (Molecular Probes, Eugene, Oreg.) or other iodocompound according to U.S. patent application Ser. No. 14/097,215.

For initial biochemical studies, the polypeptides were synthesized on a small scale in batches of less than 1 gram. After the polypeptides were cleaved from the resin and dried, 200 to 300 mg of crude material were dissolved in water, and purified on a preparative Jupiter Proteo C12 column (21.2×250 mm) (Phenomenex, Torrance, Calif.) using a gradient of acetonitrile in water containing 0.1% TFA. Fractions containing the peptide were collected and dried under vacuum. Solutions of polypeptides in water were neutralized to pH 5, and passed through a DEAE-Sephadex A-25 column (0.8×18 cm) at pH 5 to 6 to remove TFA and then eluted from a column of CM-Sephadex C-50 with NaCl to remove endotoxin, diluted with endotoxin-free standard phosphate-buffered saline (PBS), pH 7.4, or 150 mM NaCl, and filter-sterilized. Concentration was determined by the bicinchoninic acid assay (Pierce, Rockland, Ill.) using a similar dansylated polypeptide (extinction coefficient, εmM=5.7 cm$^{-1}$ at 336 nm) as standard. Additionally, the concentration of peptide was determined by a peptide extinction coefficient of 22 OD/mg/mL at 210 nm. The presence of endotoxin was assayed by gel formation with the *Limulus amebocyte* lysate (Sigma-Aldrich, St. Louis, Mo.).

Figure 3:
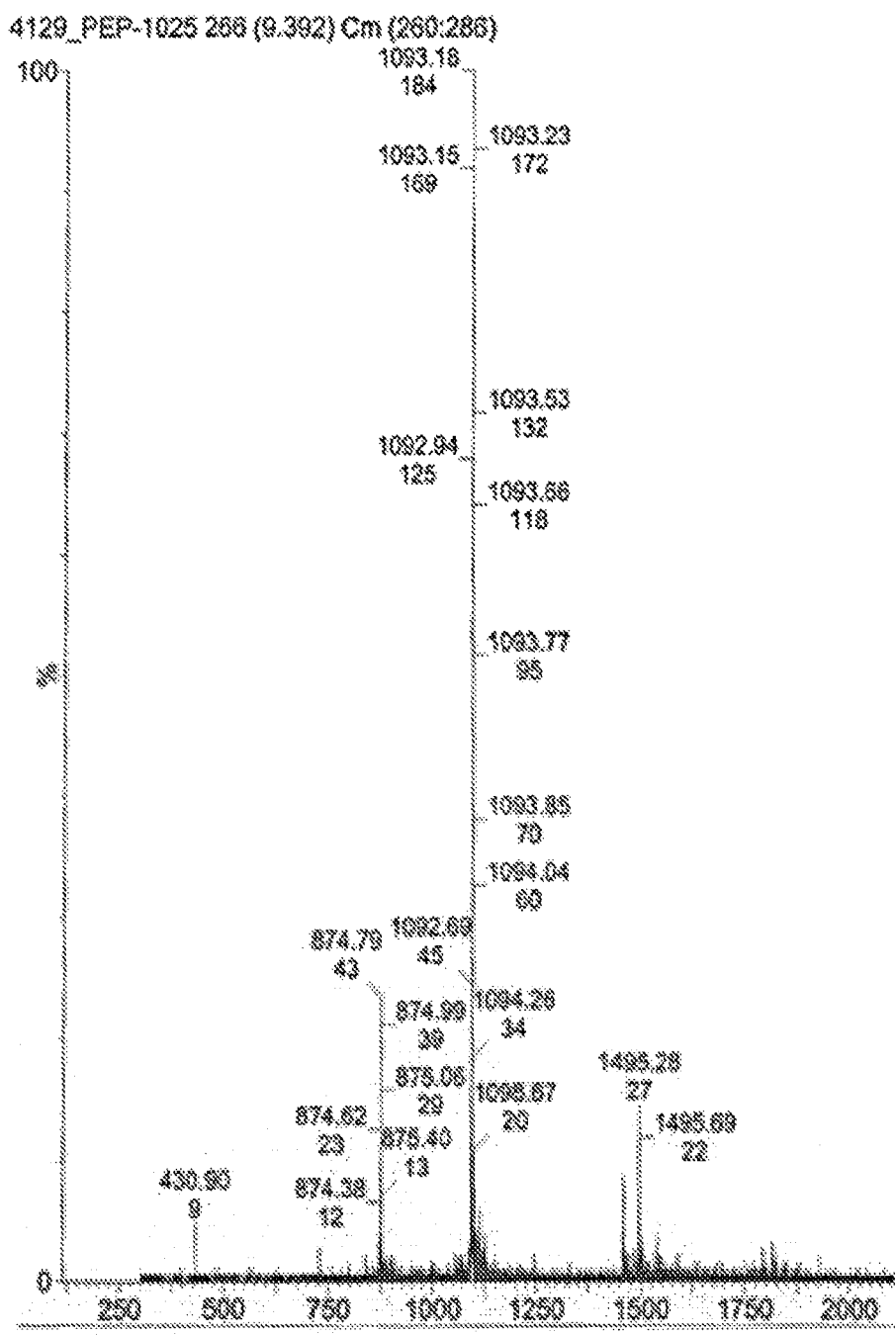
FIG. 3 is an electrospray mass spectrum of svD2. A charge on the molecule is provided by the number of hydrogen ions bound to the peptide, as indicated.

The quality of the synthetic product, including correct synthesis and purity, was assessed by matrix-assisted laser desorption/ionization (MALDI) and electrospray ionization (ESI) mass spectroscopy. Possible impurities remaining in the final product were derivatives of the main polypeptide, which may have included smaller products of incomplete synthesis or molecules with incomplete removal of blocking groups. As shown by the mass spectrum (FIG. 3), these impurities were present in very low amounts in the purified polypeptide.

Figure 4:
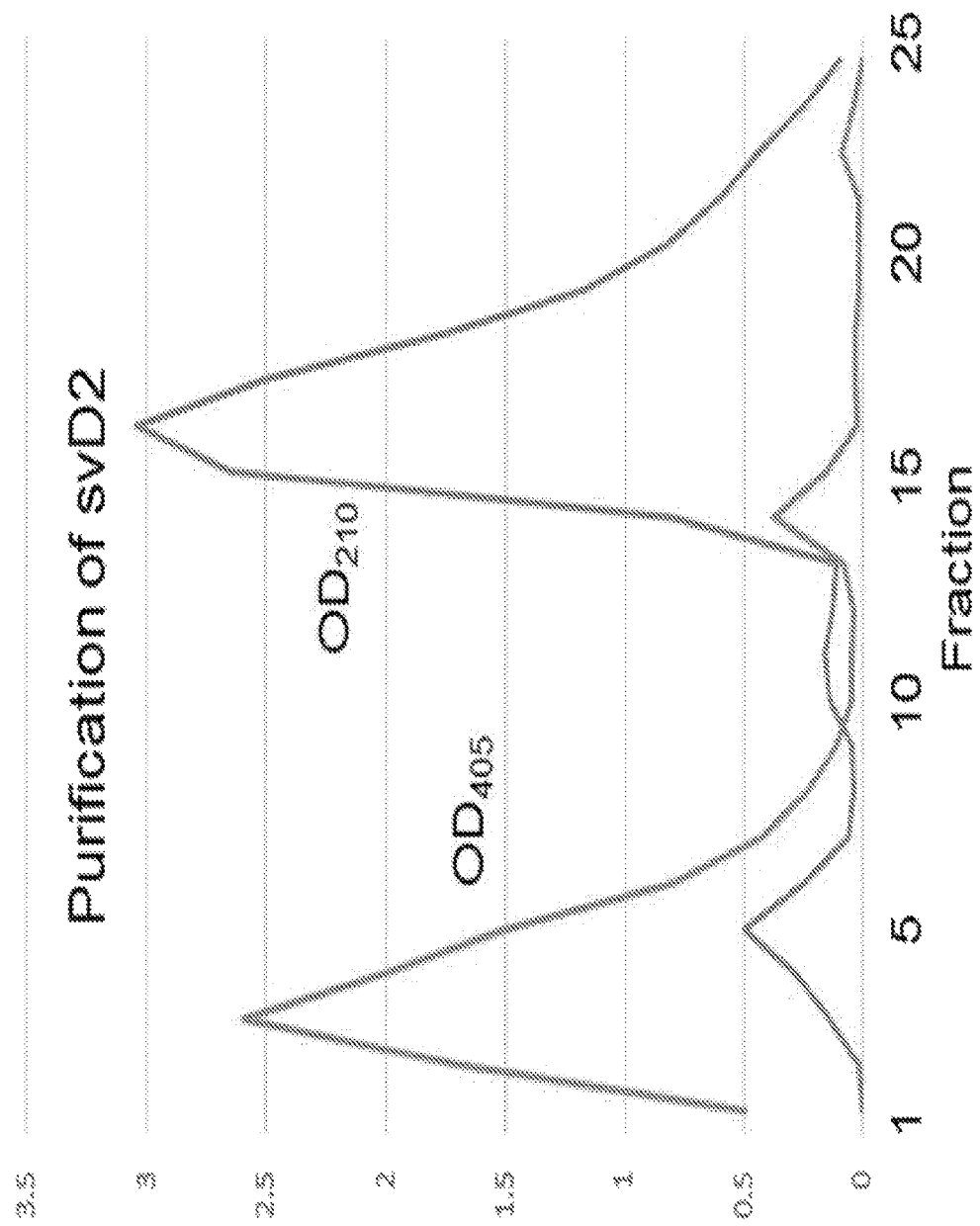
FIG. 4 is an illustration of the purification of svD2 by ion exchange chromatography on a column of CM-Sephadex C-50. Prior to application to this column, one gram of lyophilized peptide were dissolved in 3 mL 100 mM $Na_2CO_3$ and passed through a column (0.8×18 cm) of DEAE-Sephadex A-25 in 75 mM NaCl. The eluate was then applied to the CM-Sephadex column (0.8×18 cm). The column was washed with 10 mL 75 mM NaCl, 15 mL, 150 mM NaCl, then 500 mM NaCl to elute the peptide. The figure shows the pattern of elution of svD2 ($OD_{210}$) and that of endotoxin ($OD_{405}$). A small amount of endotoxin was released from the peptide with 500 mM NaCl and eluted ahead of the peptide. Biotinylated svD2 eluted with the same pattern as the untagged peptide.
Figure 5:
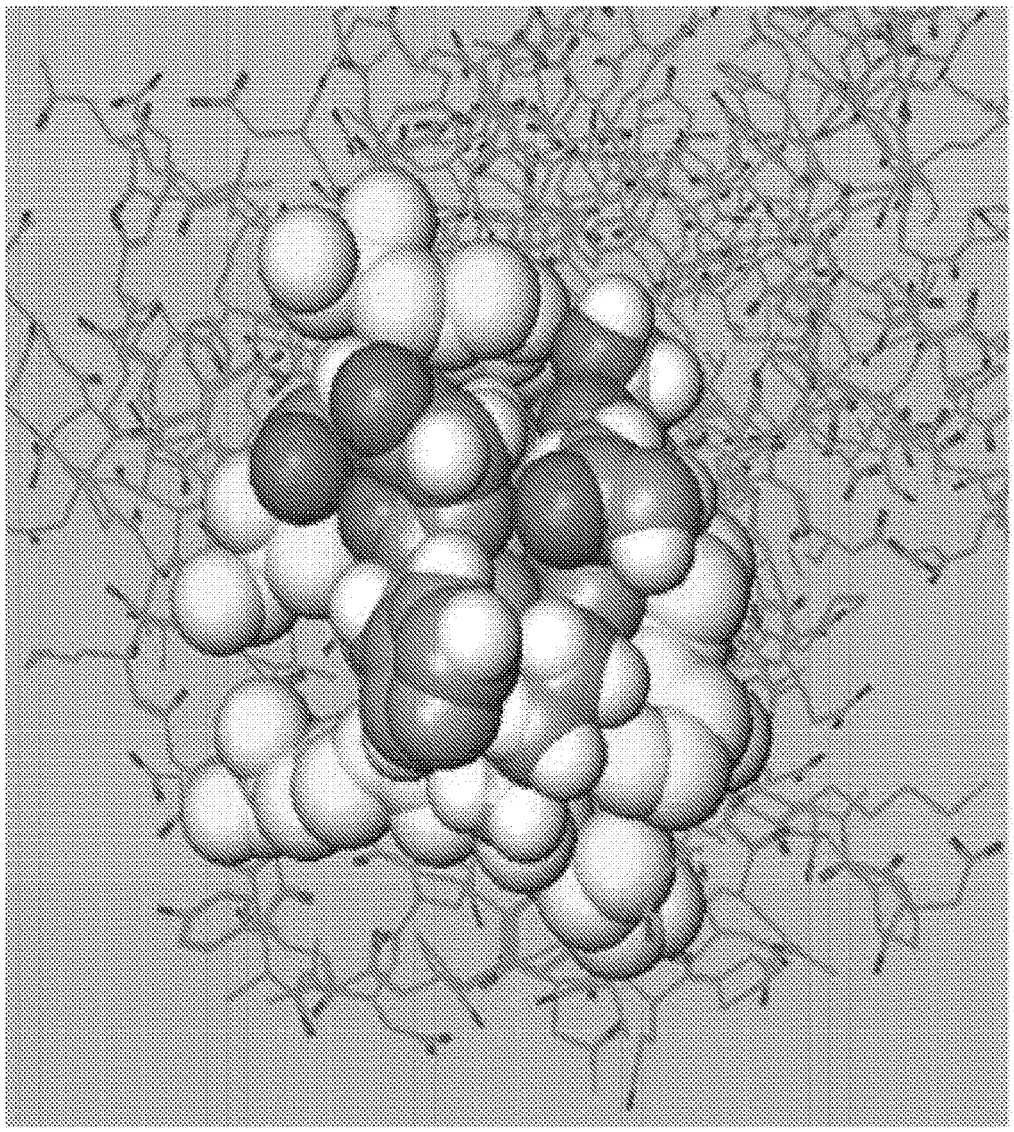
FIG. 5 show a molecular model predicting the binding of svD2 to human Galectin-1 (accession number 3OYW) ($\Delta G'$=−48 kJ/mole).

Because aspects of the biological effects of lipopolysaccharide (endotoxin) are counter to the activity of svD2, further purification of the therapeutic product was performed with ion exchange chromatography on sequential columns of DEAE-Sephadex A25 and CM-Sephadex C50 to obtain peptide free of endotoxin. The assay for endotoxin by gel formation with the *Limulus amebocyte* lysate was found to be inadequate because of imprecision of the assay and the peptide strongly bound lipopolysaccharide, which could be dissociated in solutions of relatively high ionic strength, such as provided by the concentration of salts in serum. Therefore, for final purification, the peptides were dissolved in 50 mM NaCl, neutralized to pH 5, and applied to a column of DEAE-Sphadex A25 and eluted with 50 mM NaCl. This column removed a significant portion of free endotoxin in the purified peptide product plus residual TFA. The NaCl concentration was then adjusted to 100 mM with 5 M NaCl and the peptide solution was applied to a column of CM-Sephadex C50, washed sequentially with 100 nM NaCl and 200 mM NaCl and then eluted with 500 mM NaCl. Endotoxin was assayed by the quantitative colorimetric assay from Lonza (*Limulus Amebocyte* Lysate, LAL, QCL-1000). Endotoxin was not retained on the CM-Sephadex column and endotoxin in peak fractions containing svD2 that eluted from the column in 500 mM NaCl was undetectable (FIG. 4).

Physical Properties of the Synthesized Polypeptide svD2 in lyophilized form is a white fluffy powder using trifluoroacetate (TFA) or acetate as a counterion. Net polypeptide content with and without the counter ion was approximately 88% and 73%, respectively. The remainder was likely water of hydration of the highly polar polypeptide. Solubility of the polypeptide in water is high. In the preparation of aqueous pharmaceutical compositions of the polypeptide with any of the pharmaceutically acceptable carriers described above, concentrations of the polypeptide in isotonic saline of 10 mM, and possibly somewhat higher, can be readily achieved. According to representative embodiments, therefore, the polypeptide is administered to a subject suffering from cancer in an aqueous pharmaceutical composition having a polypeptide concentration generally from about 0.1 mM to about 10 mM, typically from about 0.1 mM to about 5 mM, and a pharmaceutically acceptable carrier.

Finished Dosage Form

Aqueous pharmaceutical compositions were adjusted to desired concentrations, in the ranges described above for injection, in endotoxin-free phosphate buffered saline (PBS) at pH 7.4, or in 150 mM NaCl, and sterilized by filtration through a 0.2 micron, low-protein-binding polyvinylidene fluoride (PVDF) or polyethersulfone membrane, for example a 0.2 μm SUPOR® membrane (PALL Corporation, Port Washington, N.Y. USA). Assays demonstrated that no measurable loss of polypeptide occurred during filtration. As discussed above, a representative administration route is subcutaneous injection. According to some embodiments, the polypeptide is administered to mice in an amount generally from about 0.01 to about 5 μmole/kg body weight per dose, and typically from about 0.1 to about 2 μmole/kg body weight per dose. In a study with mice, as described below, subcutaneous injection was performed on alternate days with doses of 0.1 to 1 µmole/kg body weight per dose. In terms of polypeptide weight, representative administration amounts are generally from about 0.05 mg/kg body weight per dose to about 35 mg/kg body weight per dose, typically from about 0.1 mg/kg body weight per dose to about 15 mg/kg body weight per dose, and often from about 0.1 mg/kg body weight per dose to about 7 mg/kg body weight per dose. According to some embodiments, an administration amount from about 0.1 mg/kg body weight per dose to about 5 mg/kg body weight per dose may be optimal. For any of these ranges of dosage amounts, administration may be at least once weekly, at least twice weekly, at least three times weekly, on alternate days, or daily, over a given treatment regimen. Equivalent doses on a body surface area parameter for humans are those optimized for mice divided by a factor of 12. For example, a dose for a human of about 0.01 to 0.4 mg/kg body weight, administered subcutaneously, may be optimal. This amount could be different, and often less, when administered by a different route.

EXAMPLE 2

The polypeptide svD2, synthesized in Example 1 above, was evaluated in terms of a number of biological activities thought to correlate with its effectiveness against cancer. Human peripheral blood mononuclear cells were placed in culture overnight to obtain resting cells. svD2 was then added to the culture at a concentration of 100 nM and 4 h later the medium was collected and analyzed with an array of cytokine antibodies by RayBiotech, Inc. Cytokines in medium from treated cells that significantly differed from the amounts in medium from untreated cells are listed in Table 1.

TABLE 1

The relative levels of cytokines released by human PBMCs in response to a 4-hour treatment with 100 nM svD2.

| Cytokine | svD2 | Untreated | LPS |
| --- | --- | --- | --- |
| Eotaxin | 47 | 32 | 32 |
| Eotaxin-2 | 470 | 193 | 469 |
| IFNγ | 170 | 134 | 158 |
| ICAM-1 | 70 | 57 | 53 |
| GM-CSF | 96 | 57 | 106 |
| IL-1a | 322 | 225 | 246 |
| IL-12p70 | 117 | 90 | 89 |
| IL-15 | 137 | 97 | 104 |
| IL-17 | 21 | 5 | 10 |
| IL-21 | 130 | 50 | (IFNγ, 100) |
| IP-10 | 377 | 230 | 268 |
| MCP-2 | 97 | 56 | 177 |
| MIG | 94 | 54 | 66 |
| TNF-α | 138 | 73 | 93 |
| TNF-β | 93 | 38 | 95 |
| PDGF-BB | 82 | 43 | 56 |
| TIMP-2 | 285 | 58 | 92 |

EXAMPLE 3

The polypeptide svD2, synthesized in Example 1 above, was evaluated in pharmacological studies with mice.

Response of Peritoneal Cells

Figure 6A:
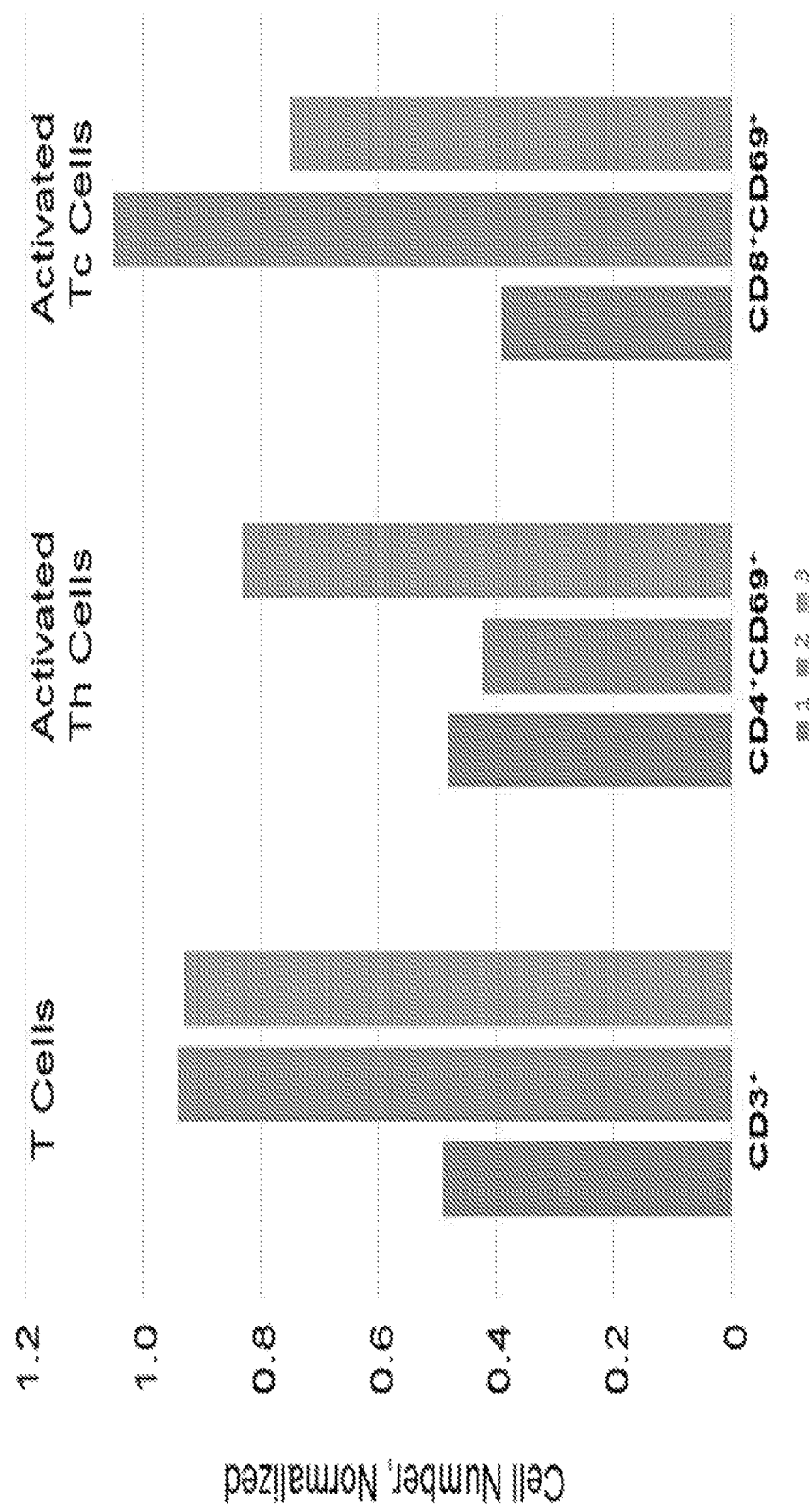
FIG. 6A-C shows bar graphs of the increases in the absolute number of immune cells in the peritoneal cavity as analyzed by flow cytometry 24 hours after each injection of 1 nmole/g doses of svD2 to C57BL/6 mice on days 1, 2 and 3. Of particular interest is FIG. 6C, which shows the increase in memory B cells, a unique property of svD2. The number of cells is indicated as a ratio of the total number of each cell type normalized to the number of cells in untreated control samples.
Figure 6B:
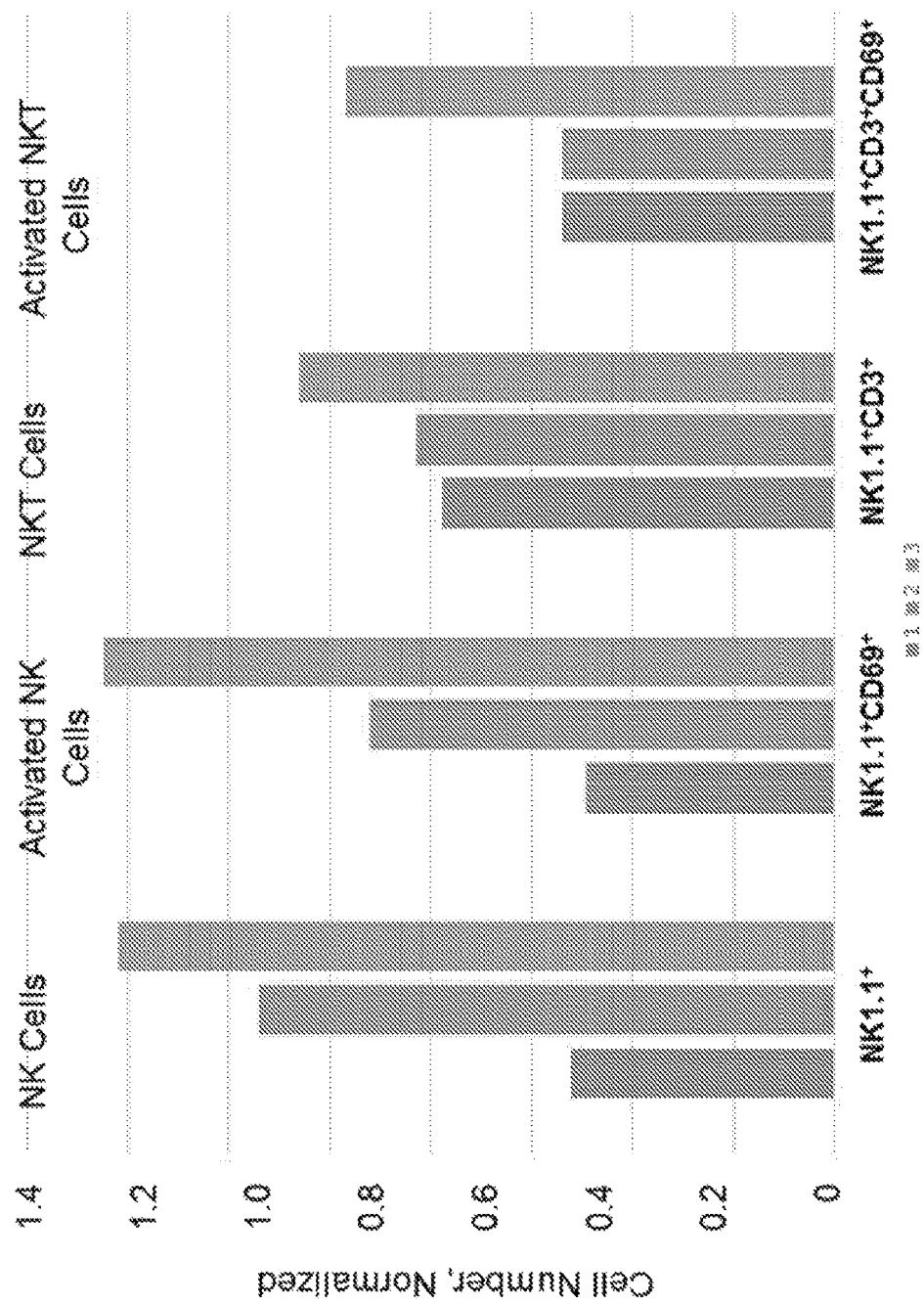
Figure 6C:
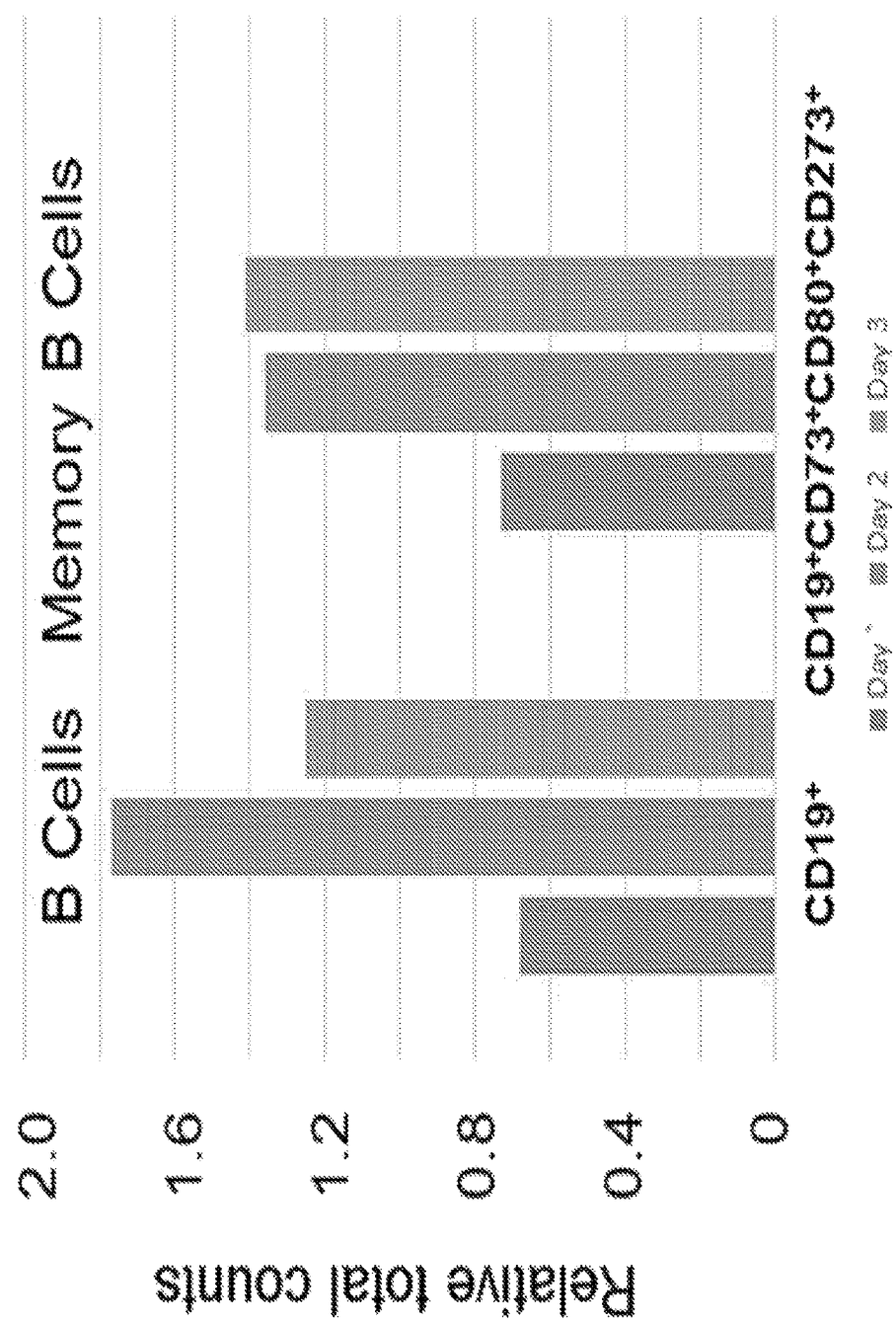

To examine whether svD2 effectively stimulates the immune system in vivo, the peptide was injected subcutaneously on alternate days into Th1-poised C57BL/6 strain mice at a dose of 1 µmole/kg. In the C57BL/6 mice, 24 hours after the second injection, peritoneal cells contained several-fold increases in mature immune cells. FIGS. 6A-C demonstrate the absolute increase in the mature cell populations normalized to the untreated samples. The figures show that in C57BL/6 mice, the changes were small 24 hours after the first injection but were highly significant 24 hours after the second injection for cells stained with antibodies against CD3 (T cells), CD8 (cytotoxic T cells), NK1.1 (natural killer cells) and CD19 (B cells) as well as markers that indicate activation of these cells (CD69). Stimulation of the immune system is demonstrated by the increased number of cells that express one or more cellular markers on lymphocytes such as B cells (CD19$^+$), memory B cells (CD19$^+$CD73$^+$CD80$^+$CD273$^+$), T cells (CD3+), activated cytotoxic T cells (CD8$^+$CD69$^+$), NK cells (NK1.1$^+$) and activated NK cells (NK1.1$^+$CD69$^+$).

Whether the peptide svD2 stimulates phagocytosis was studied in the human PBMC cultures. The cells were treated 20 h with vehicle (phosphate-buffered saline, PBS), 50 nM svD2 or 100 ng/mL IFNγ, and then challenged 1 h with microspheres. Cells were fixed with 2% formalin and washed with PBS. Beads in each cell were counted on microscope images, with 15 cells analyzed for each treatment. As demonstrated by the data in Table 2, svD2 stimulates the T and B cell adaptive arm of the immune system but does not significantly stimulate phagocytic cells.

TABLE 2

Phagocytosis of microspheres opsonized with rabbit antiserum.

| Treatment | Beads/cell (mean ± SD) | p value |
| --- | --- | --- |
| Vehicle | 1.0 ± 0.5 | — |
| svD2 | 1.3 ± 1.8 | 0.702 |
| IFNγ | 35.8 ± 12.6 | 0.00016 |

Antigenicity

The tri-lysine core of tetravalent polypeptides is immunologically silent. Examination of the amino acid sequence of svD2 using MHC binding prediction databases indicated that they are not likely to be presented by MHC class I or MHC class II molecules in humans. svD2 is not predicted to be antigenic, as indicated by RANKPEP software, and other polypeptides of this design have been shown to be non-antigenic in animals.

Toxicity in vivo

No evidence of toxicity has been detected with treated mice.

Survival of Mice Implanted with ID8 Cells

Figure 7:
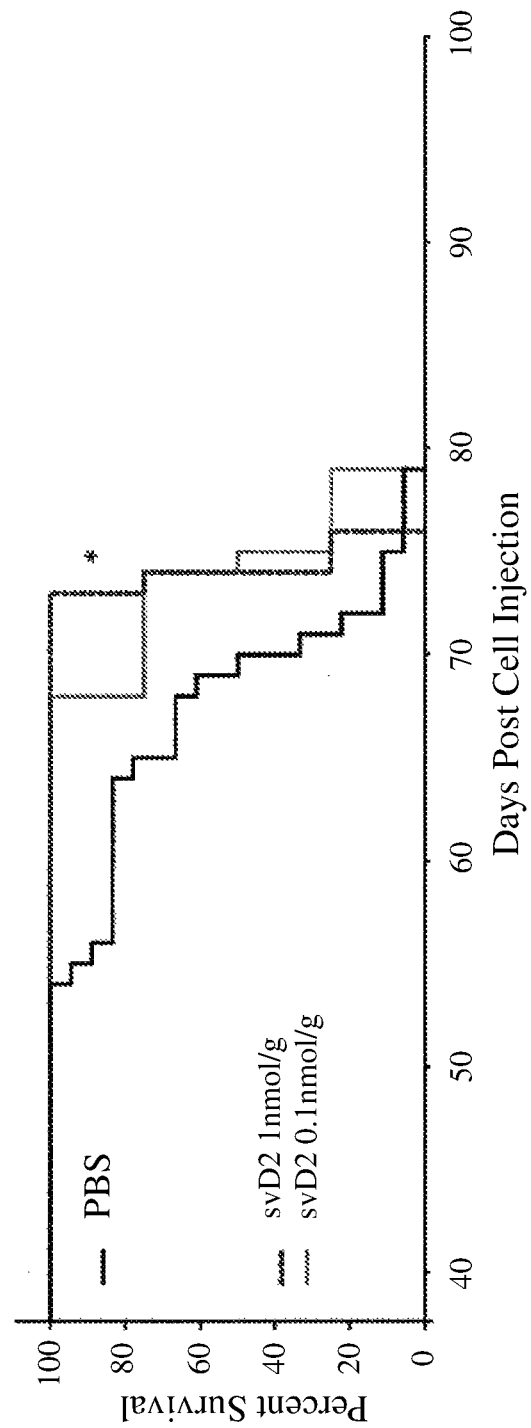
FIG. 7 shows the survival curve of female C57Bl/6 mice implanted with the ovarian cancer cell line ID8. Tumors were allowed to progress for 45 days before the animal were injected with svD2 every other day.

Female C57Bl/6 mice were implanted with ID8 cells. After allowing the cell to develop into tumors for 45 days, the animals received injections of svD2 every other day at a dose of 1 nmol/g body weight or 0.1 nmol/g body weight. Accumulation of ascites was monitored by weight of the animals as the result of expansion of the peritoneal cavity. Both of doses of svD2 improved the survival rate of mice implanted with ID8 cells (FIG. 7). Table 3 summarizes the survival data including a treatment with paclitaxel, which is a standard-of-care chemotherapeutic drug. The animals were given paclitaxel at a dose of 18 mg/kg body weight on days 45, 47 and 49 of the experiment.

TABLE 3

|  | No Treatment | PBS | svD2 (1 nmol/g) | svD2 (0.1 nmol/g) | Paclitaxel (18 mg/kg) |
|---|---|---|---|---|---|
| Number of deaths | 19 | 18 | 4 | 4 | 10 |
| Mean survival (days) | 66 | 69.5 | 74 | 74.5 | 81.5 |

CONCLUSIONS

The polypeptide svD2 was found to exhibit a number of biological activities that are believed to correlate with its demonstrated effectiveness in prolonging the survival of mice implanted with cancer cells. For example, the in vitro studies with this polypeptide showed that it (i) activated T cells, with the induction of the release of IL-21, which activates CD8$^+$ T cells, (ii) activated NK cells and (iii) induced production of memory B cells.

Overall, therefore, the observed in vitro and in vivo biological effects of the polypeptide svD2, and particularly its immunostimulant effects through activation of T and B lymphocytes and NK cells.

What we claim is:

1. A method for treating cancer, the method comprising administering to a subject having cancer a polypeptide comprising an amino acid sequence of VSNQH (SEQ ID NO:1) in an amount sufficient to treat cancer.

2. A method for increasing the survival period or probability of a subject diagnosed as having a tumor, the method comprising administering to the subject a polypeptide comprising an amino acid sequence of VSNQH (SEQ ID NO:1) in an amount sufficient to increase the subject's survival period or probability.

3. The method of claim 2, wherein the tumor comprises ovarian cancer cells.

4. The method of claim 1, wherein the polypeptide comprises the amino acid sequence of VSNQH (SEQ ID NO:1) and a spacer sequence GGGS (SEQ ID NO:3).

5. The method of claim 1, wherein the polypeptide is branched and the cancer is ovarian or melanoma.

6. The method of claim 5, wherein the polypeptide has a multivalent structure with multiple branches comprising the amino acid sequence of VSNQH (SEQ ID NO:1).

7. The method of claim 6, wherein the polypeptide has the sequence of VSNQHGGGS (SEQ ID NO:2).

8. The method of claim 5, wherein the polypeptide has a multivalent structure with multiple branches extending from lysine residues.

9. The method of claim 1, wherein the polypeptide is administered systemically to bind to receptors on immune cells.

10. The method of claim 1, wherein administration of the polypeptide does at least one of the following: stimulates production of progenitor/precursor cells in the peritoneal cavity; induces maturation and activation of immune cells in the peritoneal cavity; causes an increase in mature cells, including T and B lymphocytes, cytotoxic T cells and natural killer cells; stimulates migration of mature immune cells from the peritoneal cavity into the blood; or stimulates release of cytokines beneficial for destruction of cancer cells or an infectious agent.

11. The method of claim 1, wherein the polypeptide is administered as a complement to another therapy.

12. The method of claim 1, wherein the polypeptide is administered in an aqueous pharmaceutical composition having a polypeptide concentration from about 0.1 to about 10 mM and a pharmaceutically acceptable carrier.

13. The method of claim 12, wherein the pharmaceutical composition is administered by subcutaneous injection or by sublingual application.

14. The method of claim 12, wherein the polypeptide is administered to an adult human in an amount from about 10 µg/kg body weight to about 5 mg/kg body weight per dose.

15. The method of claim 14, wherein the polypeptide is administered in multiple doses over a treatment regimen.

16. The method of claim 1, wherein the polypeptide does not stimulate phagocytosis, based on comparison of internalization of bacterial cells by PBMCs stimulated with IFNγ.

17. The method of claim 1, wherein the polypeptide stimulates the immune system, based on increased density of one or more cellular markers on peritoneal cells.

18. The method of claim 17, wherein the markers include one or more of CD19, CD8, NK1.1, and CD69.

* * * * *